United States Patent [19]

Lara

[11] Patent Number: 4,843,319
[45] Date of Patent: Jun. 27, 1989

[54] TRANSIENT ELECTROMAGNETIC METHOD FOR DETECTING CORROSION ON CONDUCTIVE CONTAINERS HAVING VARIATIONS IN JACKET THICKNESS

[75] Inventor: Pedro F. Lara, Dallas, Tex.

[73] Assignee: Atlantic Richfield Company, Los Angeles, Calif.

[21] Appl. No.: 134,224

[22] Filed: Dec. 17, 1987

[51] Int. Cl.[4] .................... G01N 27/82; G01R 33/12; G01B 7/10
[52] U.S. Cl. ................................. 324/240; 324/71.2; 324/229
[58] Field of Search .............. 324/220, 221, 229, 230, 324/236–243, 65 CR, 71.1, 71.2, 336, 425

[56] References Cited

U.S. PATENT DOCUMENTS

| | | | |
|---|---|---|---|
| 3,229,197 | 1/1966 | Renken | 324/240 |
| 3,315,155 | 4/1967 | Colani | 324/239 |
| 3,532,969 | 10/1970 | McCullough et al. | 324/239 X |
| 3,707,672 | 12/1972 | Miller et al. | 324/239 |
| 3,745,452 | 7/1973 | Osburn et al. | 324/254 X |
| 4,194,149 | 3/1980 | Holt et al. | 324/238 X |
| 4,271,393 | 6/1981 | Hansen et al. | 324/240 |
| 4,418,574 | 12/1983 | Flournoy | 324/229 X |
| 4,611,170 | 9/1986 | Stanley et al. | 324/239 X |
| 4,717,006 | 1/1988 | Chapman et al. | 324/239 X |

OTHER PUBLICATIONS

Flora, "Deep-Penetration Eddy-Current Techniques to Detect Corrosion Under Insulation", MTI Publication No 22, Materials Technology Institute of the Chemical Process Industries, Inc., Jun. 1986.

Primary Examiner—Gerard R. Strecker
Attorney, Agent, or Firm—Geoffrey A. Mantooth; Arthur F. Zobal; James C. Fails

[57] ABSTRACT

There is disclosed a method for detecting corrosion on the walls of conductive containers wherein a transmitting antenna induces a current into a portion of the container wall and the decay of the induced current is detected by a receiving antenna, with a record of the decay of the induced current being created. The record is interpreted to determine the thickness of the container wall portion and the presence or absence of corrosion is inferred. The effects of variations in distance between the transmitting antenna and the receiving antenna and the pipe wall at one location on the pipe and between the transmitting antenna and the receiving antenna and the pipe wall at another location on the record of the decay are corrected for by examining the rate of decay of the induced current.

10 Claims, 6 Drawing Sheets

TRANSIENT ELECTROMAGNETIC METHOD FOR DETECTING CORROSION ON CONDUCTIVE CONTAINERS HAVING VARIATIONS IN JACKET THICKNESS

FIELD OF THE INVENTION

The present invention relates to a non-destructive method for detecting corrosion on electrically conductive containers such as pipelines, storage vessels, pressure vessels and the like that have variations in the thickness of a jacket, such as insulation, on said containers.

BACKGROUND OF THE INVENTION

Oil and gas pipelines located at Alaska's Prudhoe Bay are wrapped with a jacket of insulating material to prevent the rapid cooling, and provide better transportability, of oil and gas fluids. The outer surface of the insulation is covered by a metal jacket for keeping out moisture. The metal jacket is typically provided in two half portions with each portion having flanges for aiding in the retention of the jacket on the pipeline. The two half portions of the jacket are joined together at the flanges which form seams. Water occasionally enters through the jacket seams and travels through the insulation to the pipe where it causes corrosion.

Prior art methods of detecting pipeline corrosion have proven inadequate. For example, pigs with corrosion detection equipment can only be used on pipelines that have access locations; many pipelines lack such locations. Ultrasonic detection methods require removal of the metal jacket and insulation, a timely and expensive procedure. Radiography detection methods are potentially hazardous and the equipment is cumbersome, requiring impractical or inconvenient adjacent vehicular support. Furthermore, with radiography methods it is often difficult to distinguish between corrosion pits filled with corrosion products and uncorroded portions of pipe walls. What is needed then is a method of detecting corrosion through insulation and the surrounding jacket, and which method can be practiced with portable equipment.

Electromagnetic probing techniques provide such a method for detecting corrosion through insulation. In the prior art, frequency domain electromagnetic probing techniques are used to detect corrosion in aircraft fuel tanks. Frequency domain electromagnetic probing techniques utilize a small number of frequencies and measure magnitude and phase differentials between the transmitted signals and the received signals. However, because frequency domain techniques, as a practical matter, utilize only a small number of frequencies, the amount of information obtained is inherently limited, thus detracting from the accuracy of the techniques.

The application "Method for Detecting Corrosion On Conductive Containers" by Brian Spies, which application is assigned to the assignee of the present invention and which application is filed the same day as the present application, discloses time domain electromagnetic probing methods for use in detecting corrosion in conductive containers. The present application discloses a method of detecting corrosion in conductive containers wherein the distance between the antenna means and the container wall varies across the area of the conductor wall, typically due to variations in insulation thickness.

It is an object of the present invention to provide a method for detecting corrosion on insulated conductive containers, wherein said method has improved accuracy in detection and can detect corrosion through a jacket having variations in its thickness.

DESCRIPTION OF PREFERRED EMBODIMENT

Part A

Figure 1:
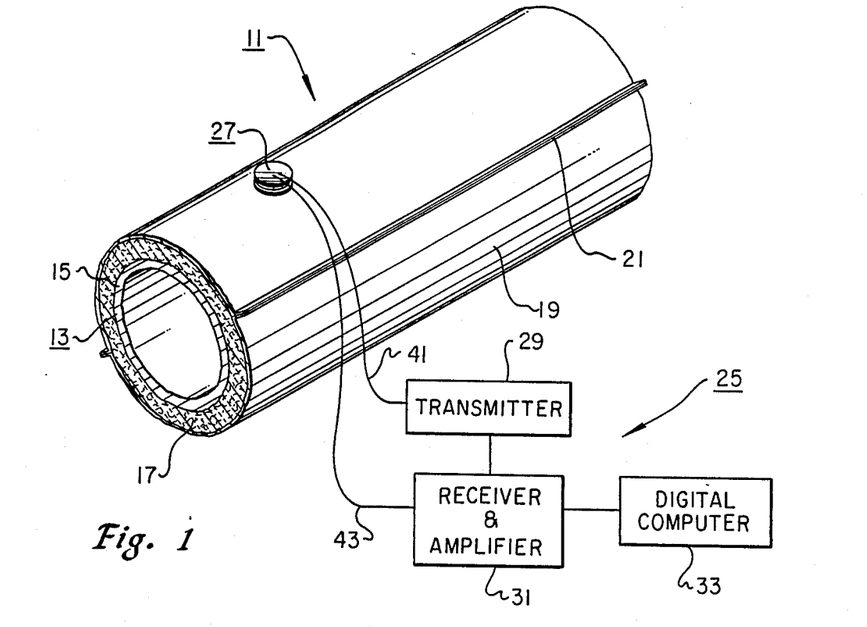
FIG. 1 is a schematic diagram showing a typcial situation in which the method for detecting corrosion in a container in accordance with a preferred embodiment of the present invention can be practiced, together with typical testing apparatus.
Figure 2:
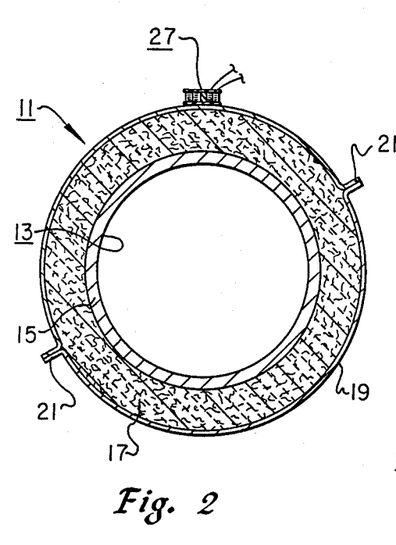
FIG. 2 is a schematic diagram showing a transverse cross-section of the pipeline of FIG. 1.
Figure 3:
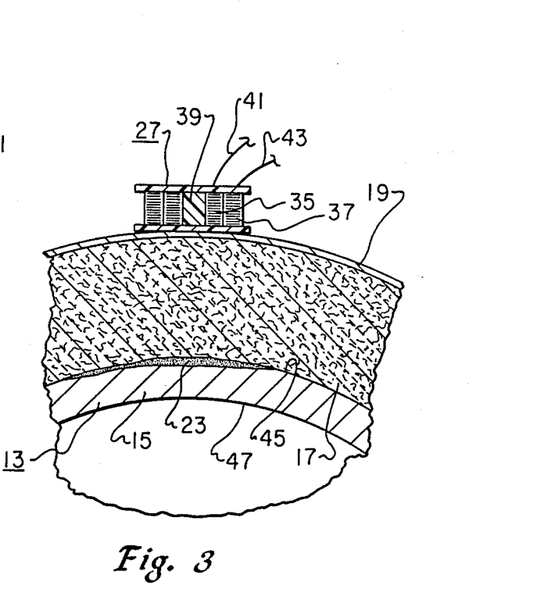
FIG. 3 is a schematic cross-sectional view showing the antenna means of FIG. 2 in detail.

In FIGS. 1-3 there is schematically shown a typical situation in which the method of detecting corrosion in electrically conductive containers 11 can be practiced, together with typical detecting apparatus 25. The method of the present invention utilizes the transient electromagnetic probing (TEMP) to detect corrosion.

The conductive container shown in FIGS. 1-3 is a portion of a pipeline 11, which is of course made up of a plurality of individual pipes 13. The pipes 13 have a diameter and the pipe walls 15 have a thickness. The pipe walls 15 are made up of an electrically conductive material such as steel.

In Alaska's Prudhoe Bay region, pipelines wrapped with insulating material 17 are used to transport oil and gas fluids. The insulation 17 is provided to prevent rapid cooling of the oil and gas fluids in the pipeline and thus provide better transportability of these fluids in the pipeline. In refineries, pipelines and vessels are commonly wrapped with insulation as a safety measure in protecting personnel from high temperatures. The insulation 17 on pipelines is typically a thermoplastic foam such as polystyrene, and has a radial thickness. Surrounding the insulation 17 is a metal jacket 19 which is provided to keep out moisture. The jacket 19 has a thickness which is much less than the thickness of the pipe wall. The metal jacket 19 has two half portions that extend longitudinally along the pipeline. Each jacket half portion has seam means in the form of flanges 21 that extend radially outward. When the jacket half portions are assembled onto the pipeline, the respective flanges 21 abut one another to form seams. The half portions are retained in place on a pipeline by securing the respective flanges together with suitable means.

In FIG. 3, the pipe wall 15 is shown to have a corrosion pit 23 adjacent to the insulation. The corrosion acts to reduce the thickness of the pipe wall, wherein it forms the pit and fills the pit with corrosion products. The corrosion that has pitted the pipe wall is caused by water that has entered the insulation between the jacket flanges 21.

Detecting apparatus 25 is provided near that portion of the pipe wall which is to be tested for corrosion and includes antenna means 27, a transmitter 29, a receiver and amplifier 31, and a digital computer 33.

The antenna means 27 nnclude a transmitting antenna coil 35, a receiving antenna coil 37 and core means 39. In the preferred embodiment, the transmitting and receiving antenna coils 35, 37 are wound onto the same core means 39, an arrangement which is hereinafter referred to as coincident (see FIG. 3). The core means 39, which is in the shape of a spool, is made of a nonmagnetic and non-conductive material such as plastic. The number of turns of the transmitting antenna coil are kept to a minimum to minimize the inductance of the transmitting antenna and to provide for an abrupt switching off of the transmitting antenna coil. In the preferred embodiment, the transmitting antenna coil 35 is made up of 120 turns of 20 to 24 gauge wire. The receiving antenna coil 37 is made up of 400 turns of 34 to 40 gauge wire. The transmitting and receiving antenna coils 35, 37 are connected to the transmitter 29 and receiver 31 by respective pairs of wires 41, 43.

The transmitter 29 which is conventional, generates a train of pulses having magnitudes of 1 to 5 amps. As discussed in more detail below, a plurality of pulses are transmitted for each location of the antenna means 27 for data enhancement purposes. The pulses have abrupt fall times on the order of 10 to 100 microseconds. The pulses of the transmitter pulse train alternate polarity to eliminate dc bias in the instrumentation. The duration of each pulse is sufficiently long to stabilize the pulse magnitude so that there are no induced currents in the pipe wall before the end of the pulse. The transmitter 29 repeats the pulses at a repetition rate that allows all of the necessary data to be obtained for each pulse. For example, a thick pipe wall requires more time to obtain data than does a thinner pipe wall because the induced current takes longer to diffuse in the thick pipe wall. Thus, the repetition rate of pulses will typically be slower for thick pipe walls than for thinner pipe walls.

The receiver and amplifier 31 is a broad band instrument with a wide (5 or 6 orders of magnitude) dynamic range. The receiver 31, which has an A/D converter, samples the signal at a constant rate and integrates the signal over a time window or channel. The duration of the time windows increases with time. The transmitter 29 and the receiver and amplifier 31 are conventional. In practice it has been found that the SIROTEM transmitter, receiver and amplifier unit manufactured by Geoex Pty. Ltd. of Adelaide, Australia, works well. The battery operated SIROTEM unit is portable, a characteristic which allows ease of use when surveying pipelines in the field.

The digital computer 33 is a conventional portable computer with sufficient memory capacity to record the data.

The method of detecting corrosion on a conductive container of the present invention will now be described. As mentioned earlier, the method of the present invention utilizes transient electromagnetic probing (TEMP). TEMP allows the remote prorbing of a conductor by inducing a current into the conductor and then analyzing the decay of the current.

First, the antenna means 27 is placed on the jacket 19 so as to be in proximity with the near surface 45 of the portion of the pipeline 11 that is to be investigated. Suitable means (not shown) are used to secure the antenna means 27 in position so as to minimize any motion of the antenna means over the investigated pipe wall portion. The transmitting antenna coil 35 is then energized by the transmitter 29 with a pulse. As described above, the transmitting antenna coil 35 is energized for a sufficient period of time to stabilize the pulse magnitude, thereby insuring no eddy currents are induced into the pipeline 11. Then, the transmitting coil 35 is abruptly de-energized by the transmitter by having the pulse fall off rapidly to zero magnitude. This abrupt de-energization of the transmitting antenna coil 35 induces eddy currents into the conductors located near the coil; namely the jacket 19 and the pipe wall 15. The eddy currents, which decay and diffuse away from the antenna means 27 inside of the respective conductors, create a magnetic field that is detected as a time-varying voltage in the receiving antenna coil 37. As soon as the transmitting antenna coil is de-energized, the receiver 31 is then switched on. The receiving antenna coil 37 detects the presence of and the decay of the induced eddy currents in the conductors. The eddy currents are gradually dissipated within the conductors by resistive heat losses. The rate of diffusion is dependent on the conductivity and thickness of the conductor. The receiver 31 samples the signal as detected by the receiving antenna coil 37, whereupon it is amplified to a suitable level and sent to the digital computer 33 for storage and processing. The receiver 31 measures the signal from the time the eddy currents are first induced into the conductors until the signal becomes indistinguishable from noise. The level of noise is reduced by minimizing any motion of the receiving antenna coil 37 relative to the conductors. The received signal is unprocessed data and forms a record in the computer 33 of the decay of the induced currents in the conductors. The transmitting and receiving procedure is repeated many times with the antenna means 27 in the same location to increase the signal-to-noise ratio.

Figure 4:
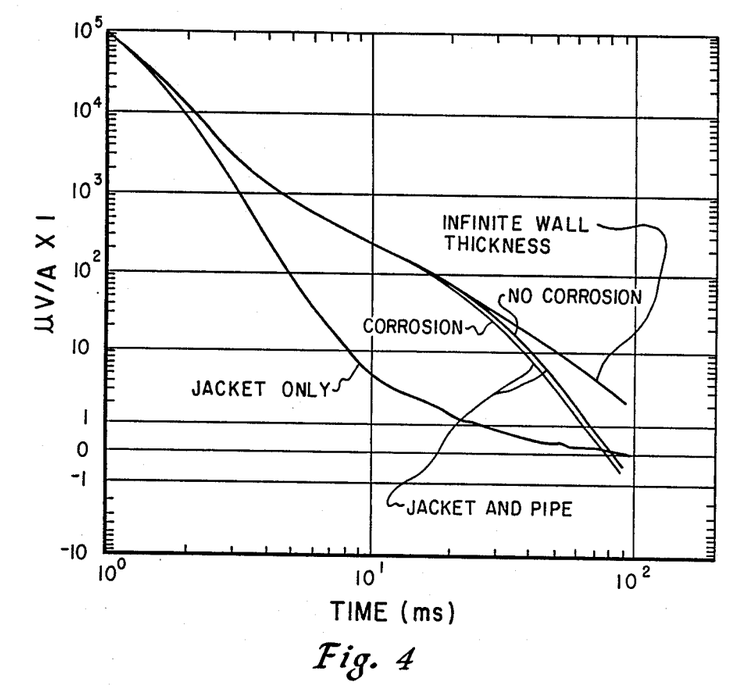
FIG. 4 is a graph showing the time domain response curves of various conductors, obtained by the transient electromagntric probing (TEMP) method of the present invention.

The data is then processed by computer data processing means into a suitable format for interpretation. The first steps in the processing of the data involve the normalization of the received signals and the summing and averaging of the received signals. Because the transmitter 29 in the preferred embodiment is battery operated, the magnitude of the transmitter current is subject to variation. The effects of variation in magnitude in the data are removed by normalizing the received voltage to the transmitted current. The summing and averaging of the received signals for a particular antenna means location serves to increase the signal-to-noise ratio. In particularly noisy environments, as an alternative to summing and averaging, selective stacking can be used to eliminate noisy transients. The result of this initial data processing is a time-varying response curve such as shown in FIG. 4. (FIG. 4 illustrates response curves for various conductors.)

The response curves may be interpreted in accordance with methods which will now be described, with reference to FIGS. 4-8d. Referring in particular to FIG. 4, the presence or absence of corrosion on a conductor wall is inferred by examining the shape of the various response curves which have been taken over the area of interest. The shape of each response curve depends in part on the thickness of the conductor wall. For example, the magnitude of the response curve of an infinitely thick conductor wall decays at a fairly even rate (on a log-log graph), resulting in a fairly straight response curve, whereas the response curve of a conductor having a finite wall thickness begins to break at some point into a more pronounced downward direction than before and decays at a faster rate. This breaking phenomenon is attributed to the induced currents diffusing to and reaching the far surface 47 of the conductor wall. Response curves for thin conductor walls break at earlier times than do response curves for thicker conductor walls.

Because corrosion reduces the thickness of a conductor wall, the presence or absence of corrosion can be inferred by comparing the shape of the response curve for the investigated pipe wall portion to the shape of the response curve for an uncorroded portion of the same type of pipe. For example, in FIG. 4, the two response curves labeled "corrosion" and "no corrosion" are taken from the same pipe. The "no corrosion" response curve is taken from an uncorroded portion of the pipe and is used as a reference, while the "corrosion" response curve is taken from a different portion of the same pipe, which different portion has a pit to simulate corrosion (with the antenna means located at the same distance from the pipe wall, for both response curves). At about 17 ms (milliseconds), the "corrosion" response curve breaks into a more pronounced downward direction and begins to decay at a faster rate than before. The "corrosion" break point occurs at an earlier time than does the "no corrosion" break point (at about 25 ms), indicating that the conductor wall represented by the "corrosion" response curve is thinner than the conductor wall represented by the "no corrosion" response curve.

Figure 5:
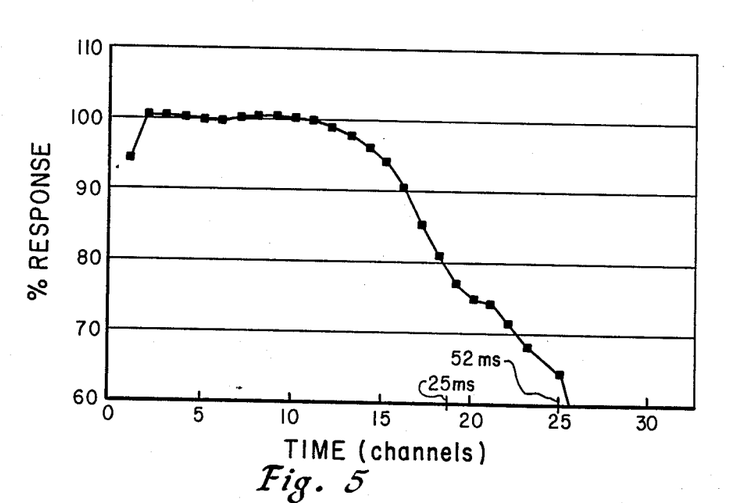
FIG. 5 is a graph of the response curve of a pit in a pipe wall, with the response curve obtained by computing the ratio of the "corrosion" to the "no corrosion" response curves of FIG. 4.

Referring now to FIG. 5, the "corrosion" and "no corrosion" response curves of FIG. 4 are compared by plotting the ratio of the two curves as a percent response curve, using the "no corrosion" response curve as a reference. The percent response curve highlights the differences between the "corrosion" and the "no corrosion" response curves. By examining the late time portions of the percent response curve (from about 17-20 ms on, which is about when the "corrosion" response curve of FIG. 4 begins to break sharply downward), one can see that the "corrosion" response curve deviates 20 to 30 percent from the "no corrosion" response curve. This 20 to 30 percent difference clearly indicates a difference in wall thickness between the corroded portion of the pipe and the uncorroded portion of the pipe.

In FIG. 4, the response curve labeled "jacket only" is that taken from the metal jacket 19, without the pipe 13. The "jacket only" response curve decays very rapidly so that by the relatively late time of 20 ms, the jacket 19 contributes very little to the total response. This is because the wall thickness of the jacket is much smaller than is the thickness of the pipe wall, so the currents diffuse much more rapidly in the jacket. Thus, for those portions of the "jacket and pipe" response curves that are of interest in locating corrosion (that is the later times), the effect of the jacket can be ignored.

Figure 7:
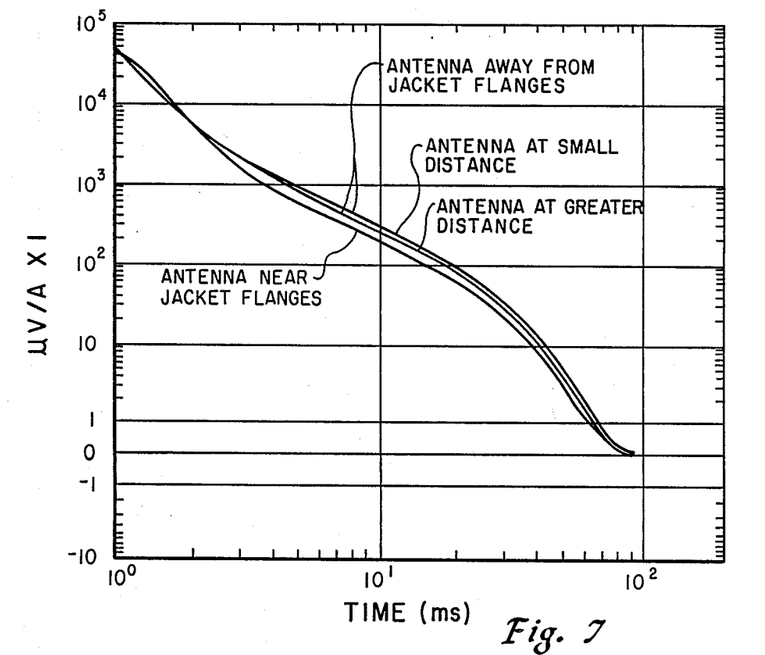
FIG. 7 is a graph showing the effects of the jacket flanges and of variations in antenna means height on time domain responses of pipe walls.

Responses measured near jacket flanges are affected quite strongly by the jacket flanges at all times, as shown in FIG. 7. A response measured near jacket flanges can be corrected to remove the effects of the jacket flanges by normalizing the affected response curve to a reference response curve obtained away from the jacket flanges. As shown in FIG. 7, an effect of the jacket flanges on the response curve is a generally parallel shift in a downward direction in the intermediate and late time ranges (later than about 4 ms). That is to say that in the intermediate and late time ranges, the affected response curve is generally parallel to the reference response curves. The affected response curve is corrected by normalizing the affected response curve to the reference response curve in the intermediate time range.

FIG. 7 also serves to illustrate the effect that variations in distance between the antenna means and the pipe wall at one location on the pipe and between the antenna means and the pipe wall at another location on the pipe can have on responses. Such variations in distance result from non-uniform thicknesses of the insulation between the pipe wall and the jacket. Increasing the distance of the antenna means from the pipe wall causes the magnitude of the response to decrease at intermediate and late times, which decrease in magnitude shows up as a generally parallel shift. The responses can be corrected to remove the effects of variations in distance by normalizing the response curves to a reference response curve obtained with the antenna means at some known distance, in the intermediate time range.

The antenna means 27 gives a reading of the average conductor wall thickness over a search area. The size of the search area depends upon antenna size, antenna configuration and the duration of the receiver measuring time after each transmitter pulse. The search area of the antenna means increases with larger antenna sizes or with longer measuring times. In the preferred embodiment, the antenna means 27 has a diameter of about 3 inches. For a 10.5 inch pipe, the search area is about 12 inches in diameter.

Figure 8A:
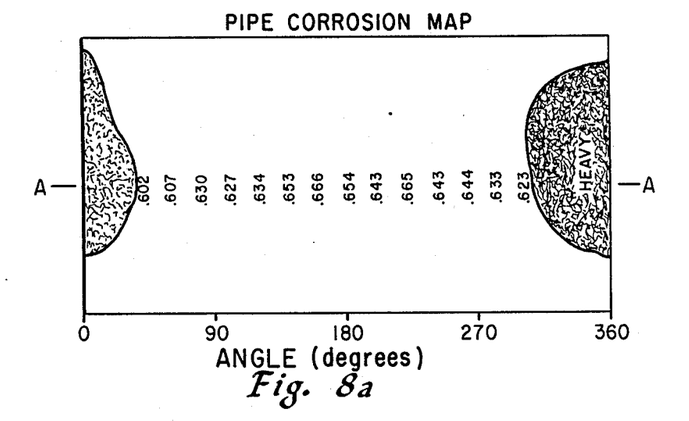
FIG. 8a is a circumferential map of a portion of a pipe showing both the location of corrosion and ultrasonic wall thickness measurements.

In the usual case, the portion of the pipeline that is to be investigated for corrosion is much larger than the search area of the antenna means. Therefore, a typical pipe survey requires the antenna means to be moved to new locations to complete the survey. In FIGS. 8a through 8d there are shown a corrosion map of a pipe section and corresponding TEMP surveys or profiles along line A—A of the pipe section. In obtaining the TEMP profiles of FIGS. 8b through 8d, the antenna means was positioned at various locations along line A—A. In FIG. 8a, the numbers along line 8a indicate ultrasonic point measurements of the wall thickness (in inches) and the shaded areas indicate heavy corrosion, wherein the thickness of the pipe wall is less than for the unshaded areas. The map shows that the pipe wall along line A—A is thickest around 180° and gets thinner moving towards 0° and 360°.

Figure 8B:
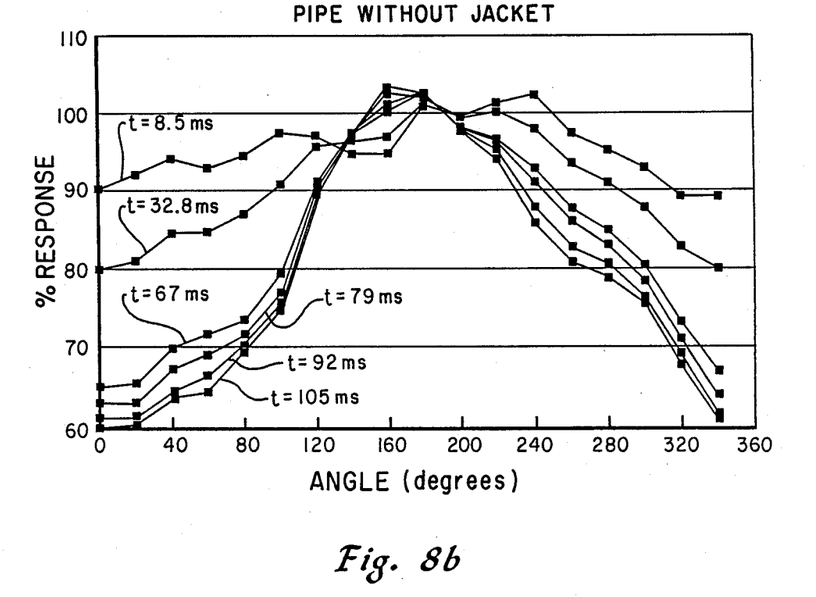
FIG. 8b is a graph showing transverse TEMP profiles of the unjacketed pipe of FIG. 8a, taken along line A—A.

FIG. 8b shows TEMP profiles of the pipe of FIG. 8a along line A—A, without a metal jacket. In FIG. 8b only those values of the response curve at selected discrete instances of time for each antenna means location are plotted. The response curve values at equivalent instances of time are then connected together to form a TEMP profile. Thus, for each antenna means location, the response curve values at time=8.5 ms, 32.8 ms, 67 ms, 79 ms, 92 ms, and 105 ms are plotted, forming respective TEMP profiles of pipe wall thickness. Each TEMP profile is normalized to the TEMP response obtained over the thickest portion of the pipe. As can be seen in FIG. 8b, the TEMP profiles show that in moving away from 180° in either direction (towards 0° and towards 360°) the pipe wall thickness lessens and is thinnest around 0° to 60° and 320° to 360°. The late time TEMP profiles (67 ms and greater) in particular clearly show the reduced wall thickness, corresponding with the pipe corrosion map of FIG. 8a.

Figure 8C:
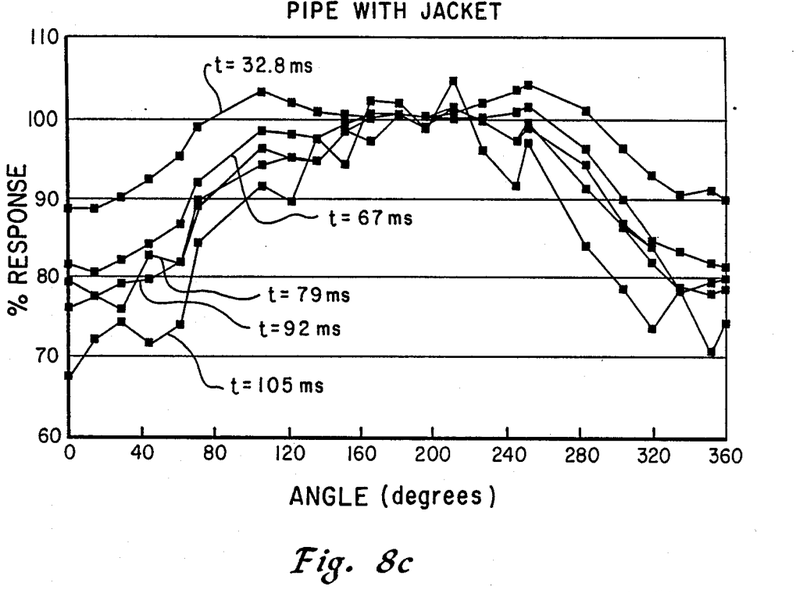
FIG. 8c is a graph showing transverse TEMP profiles of the jacketed pipe of FIG. 8a, taken along line A—A, with the TEMP profiles corrected for the effects of the jacket flanges.

In FIG. 8c, there are shown TEMP profiles of the pipe of FIG. 8a along line A—A, but with a metal jacket. The TEMP profiles of FIG. 8c were obtained in the same manner as the TEMP profiles of FIG. 8b. The jacket flanges, which are located at approximately 95° and 270°, have caused reductions in the amplitudes of the TEMP profile portions near the flanges. The TEMP profiles of FIG. 8c have been corrected to reduce the effects of the jacket flanges by normalizing the responses measured near the jacket flanges to a response measured away from the jacket flanges. The responses are normalized in the intermediate time range (3-6 ms) and the late times (32 ms and greater) are then analyzed. (In FIG. 8d there are shown the TEMP profiles of FIG. 8c before the profiles have been corrected for the effects of the jacket flanges.) There is a good correlation between the TEMP profiles of FIG. 8c and the corrosion map of FIG. 8a. The TEMP profiles of FIG. 8c show that the pipe wall is reduced in thickness around 0° to 60° and 320° to 360°, thus leading to an inference of corrosion at those locations.

FIGS. 8a through 8d illustrate an advantageous difference of the TEMP method over the ultrasonic method. The ultrasonic method makes point measurements, requiring a large number of measurements, whereas the antenna means of the TEMP method has a large search area requiring fewer measurements. While the ultrasonic measurements in FIG. 8a are essentially confined to line A—A, the TEMP measurements encompass portions of the pipe extending for a few inches to either side of line A—A. Furthermore, ultrasonic measurements must be made on the bare pipe, while TEMP measurements can be made on the jacket.

Figure 8D:
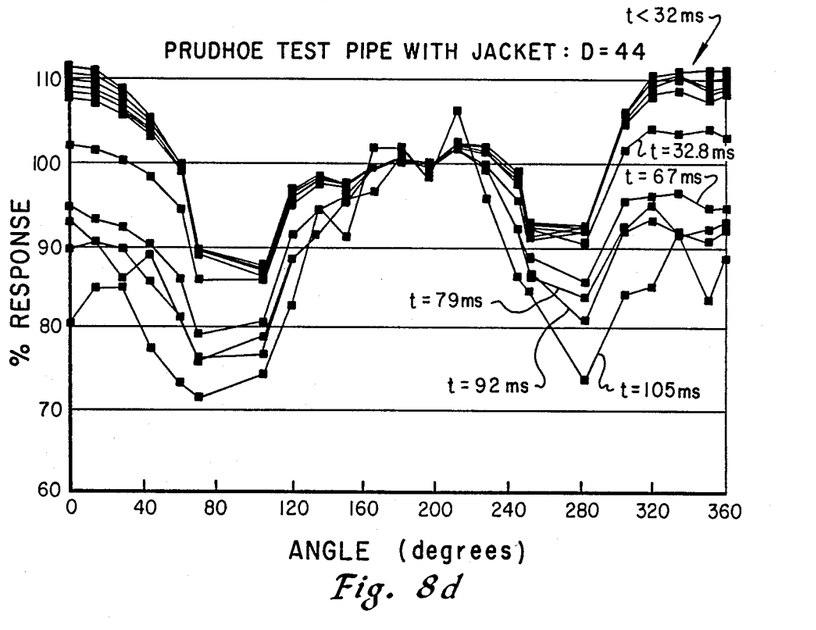
FIG. 8d is a graph showing the same TEMP profiles as in FIG. 8c, but uncorrected for the effects of the jacket flanges.

For TEMP profiles such as are shown in FIGS. 8b-8d, the effects on the responses due to the variations in distance between the antenna means and the pipe wall, which variations are caused by moving the antenna means from one location on the pipe to another location, can be corrected for by creating reference response curves with the antenna means placed at a number of known distances from the pipe wall. The intermediate times of the response curves having distance error are then normalized to the intermediate times of the respective reference response curves.

Figure 6:
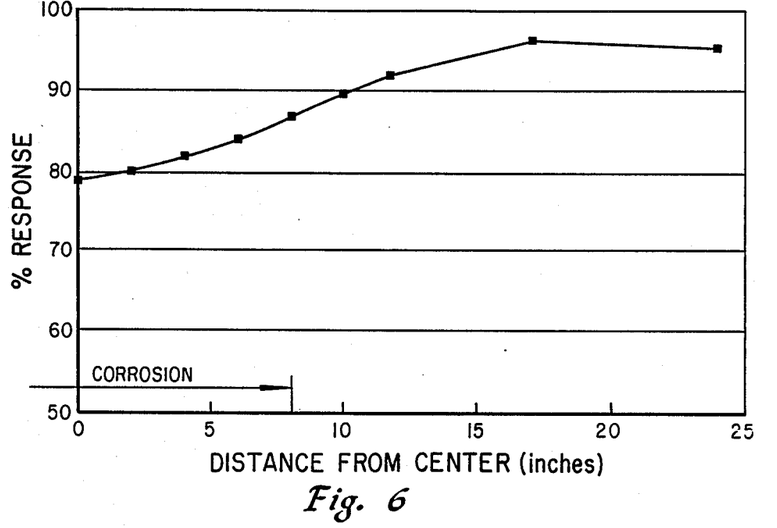
FIG. 6 is a graph showing a longitudinal cross-sectional TEMP profile of the pit of FIG. 5, with the profile being obtained by averaging the late time responses at each antenna means location.

In FIG. 6, there is shown a TEMP profile of the corrosion pit of FIG. 5. The TEMP profile is obtained by moving the antenna means to a plurality of locations and averaging the responses for the 25 to 52 ms time window at each antenna means location. The physical extent of the corrosion pit is indicated at the bottom left corner of the graph, which shows the pit to have a radius of about 8 inches. The TEMP profile of FIG. 6 shows a good correlation to the physical profile. From about 17 inches on, the TEMP profile shows a slight decrease in magnitude due to the induced currents interacting with the nearby pipe end.

Another method of interpretation of the response curves of FIG. 4 involves examining the time at which the far surface 47 of the pipe wall is initially manifested in the response curve. This time is referred to as the "critical time", and is that point where the response curve begins to break into a more pronounced downward direction than before, as discussed hereinbefore (see FIG. 4). The wall thickness of the pipe is proportional to the square root of the critical time. The constant or factor of proportionality is dependent on the geometry and the conductivity of the pipe, and may be determined by making a determination of the critical time of a particular thickness of the pipe.

The method of the present invention can be used to make quantitative measurements of wall thickness, once the instruments and data have been calibrated on pipes of known thickness and conductivity. Once the actual wall thickness of the investigated pipe is known, comparison to the manufactured wall thickness leads to a determination of wall loss due to corrosion on the investigated pipe.

Part B

Another method for correcting error in the responses due to variations in distance between the antenna means and the pipe wall from one location along the pipe to another location will now be described, with reference to FIGS. 9 and 10.

Figure 9:
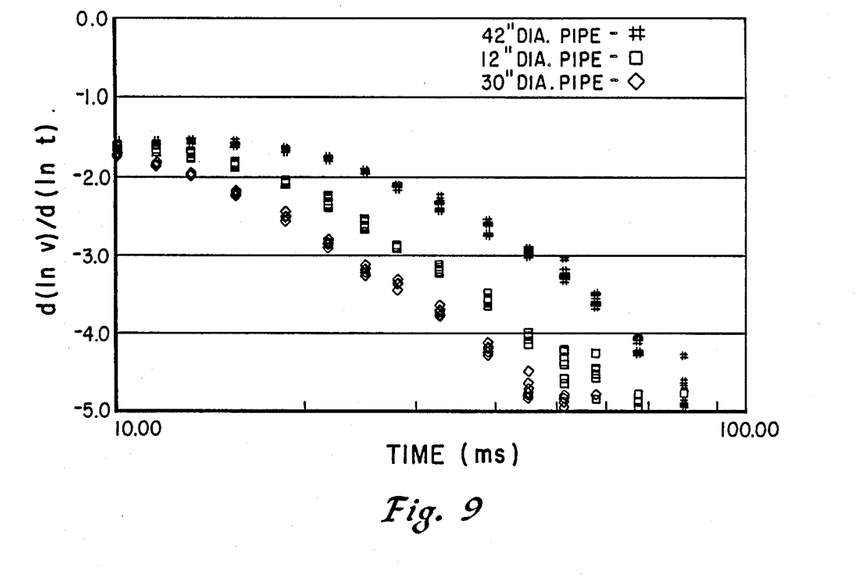
FIG. 9 is a graph showing a plurality of time domain response curves for various pipes, there being shown a plurality of response curves for each pipe taken at different locations on each pipe, with the response curves corrected for variations in distance between the antenna means and the pipe walls.
Figure 10:
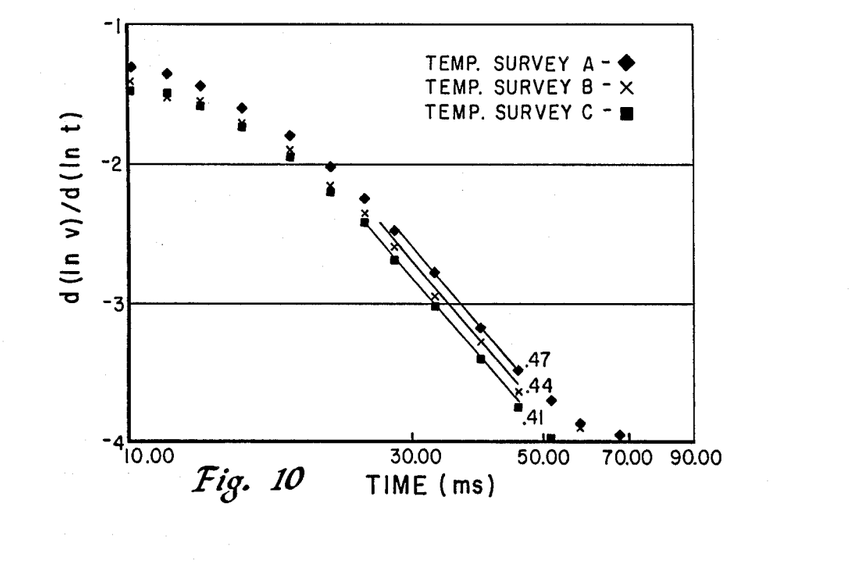
FIG. 10 is a graph showing a plurality of response curves for a pipe taken at different locations on the pipe, with the response curves corrected for variations in distance between the antenna means and the pipe wall, there being shown a nomogram superimposed on the corrected response curves.

In FIG. 9 there are shown a plurality of TEMP response curves (plotted as discrete values instead of as continuous values) that have been corrected for effects due to variations in distance between the antenna means and the pipe walls. FIG. 9 illustrates the corrected response curves for a forty-two inch diameter pipe (with a pipe wall thickness of 0.438 inches), a twelve-inch diameter pipe (with a pipe wall thickness of 0.406 inches), and a thirty-inch diameter pipe (with a pipe wall thickness of 0.344 inches). For each pipe, numerous TEMP surveys were taken at different locations along the pipe. The TEMP surveys were obtained through insulation 17 and a metal jacket 19. The thickness of the insulation along each pipe varied as much as fifty percent, thus causing the distance between the antenna means and the pipe walls to vary by the same amount.

The record of the decay of induced current in a pipe wall (as shown by the respective designated response curves of FIG. 4) is corrected for the variations in distance by determining with respect to time the rate of decay of the induced current. Correcting for variations in distance by determining the rate of decay of induced current recognizes the phenomenon that variation in distance between the antenna means and the pipe wall affects the magnitude of the response, but does not affect the rate of decay of the response. In FIG. 9, the corrected response curves shown illustrate the respective rates of decay of uncorrected TEMP survey responses obtained from the pipes. The rates of decay were obtained by taking the logarithmic derivative (d(ln V)/d(ln t); where V is the received voltage and t is time) of the uncorrected TEMP survey responses. (Central difference numerical methods were used to obtain the graphs of FIGS. 9 and 10.) As can be seen, in spite of the variations in insulation thickness, the vertical scatter among the corrected TEMP surveys for each pipe is small, and is in fact due to variations in pipe wall thickness. Thus, by determining the rates of decay of the responses, the effects of variation in distance between the antenna means and the pipe wall have been corrected for. The presence or absence of corrosion in the pipe wall is inferred by the interpretation methods discussed hereinabove.

The rate of decay correction method also allows the quantitative determination of wall thickness. As the induced currents diffuse through the conductor walls from the near surface 45 (see FIG. 3), the responses decay at a constant logarithmic rate of about $-1.5$. Then, as the induced currents begin to interact with the far surface 47 of the conductor wall, the responses decay at increasing rates. The time of departure of a response decay rate from the constant logarithmic rate of about $-1.5$ is a function of the pipe wall thickness and the pipe diameter. The corrected responses of thinner pipe walls break downwardly at an earlier time than do the corrected responses of thicker pie walls. Increases in pipe diameter cause the responses to break downwardly at later times. After the induced current reaches the far surface of the pipe wall, the rate of decay of the response approaches asymptotically a constant second derivative. This asymptotic portion of the rate of decay of the response is independent of the thickness of the pipe wall or the pipe diameter and has been determined empirically to be:

$$d(\ln V)/d(\ln t) \approx A - 2.17 \ln t;$$

where A is a function of pipe wall thickness, pipe diameter, and pipe metallurgy. The asymptotic characterisic of the rate of decay of the response, coupled with the time of departure of a response decay rate being dependent upon the pipe wall thickness allows the construction of nomograms that can be superimposed on the corrected response curves. The nomograms are constructed from numerous reference records which are created by inducing current into pipe walls of known thickness and substantially similar diameters. In FIG. 10, there is shown a nomogram consisting of straight lines superimposed on corrected response curves (TEMP surveys A, B, and C) obtained from various locations along a corroded eight-inch diameter pipe. Thus, it can be seen by extrapolatory comparisons between the individual TEMP surveys and the nomogram that the pipe wall portion that was probed with TEMP survey A had a thickness of about 0.46 inches, the portion that was probed with TEMP survey B had a thickness of about 0.43 inches, and the portion that was probed with TEMP survey C had a thickness of about 0.41 inches. From these quantitative pipe wall thickness measurements, the presence or absence of corrosion on the pipe wall can be inferred.

An important aspect of the present invention is the increased accuracy of detection of corrosion on conductive walls over prior art eddy current or TEMP methods. The present invention operates in the time domain rather than in the frequency domain. In the time domain, all the information needed to probe a conductor wall for accurate detection is obtained with one transmitter pulse. Each pulse contains an infinite number of frequencies. With frequency domain methods however, only a few frequencies are used to probe a conductor wall, resulting in a limited amount of information from which wall thickness is to be determined.

Another important aspect of the present invention is the ability to detect corrosion through insulation of varying thickness. By examining the rate of decay of the induced current, the efffects of variation in distance between the antenna means and the pipe wall at one location on the pipe and between the antenna means and the pipe wall at another location on the pipe on the responses are corrected for.

Although the method of the present invention has been described for use in detecting corrosion on pipelines, the method may also be used to detect corrosion on the electrically conductive wall of other types of container means such as storage vessels and pressure vessels. In addition, the method of the present invention can be used on uninsulated as well as insulated container means.

The antenna means can have the transmitting antenna and receiving antenna configured in arrangements other than the coincident arrangement described herein. One such arrangement has the transmitting antenna separate but coplanar with the receiving antenna. Another arrangement has a plurality of receiving antennas located within a large transmitting antenna loop.

Although this invention has been described with a certain degree of particularity, it is understood that the present disclosure is made only by way of example and that numerous changes in the details of construction and the combination and arrangement of parts may be resorted to without departing from the spirit and the scope of the invention, reference being had for the latter purpose to the appended claims.

What is claimed is:

1. A method of detecting corrosion in walls of container means, said walls being electrically conductive and having near surface and far surfaces, comprising the steps of:
   a. placing transmitting antenna means and receiving antenna means in proximity of the near surface of that portion of the container means wall which is to be investigated for corrosion;
   b. energizing the transmitting antenna means with current;
   c. abruptly de-energizing the transmitting antenna means so as to induce current into the container means wall portion;
   d. detecting the presence of and the decay of said induced current in said container means wall portion with the receiving antenna means;
   e. creating a record of the decay of said induced current in said container means wall portion over a period of time, said record having intermediate and late time ranges, wherein said record of said induced current is influenced by variations in distance between said transmitting antenna means and said receiving antenna means and said container means wall caused by moving said transmitting antenna means and said receiving antenna means from one location to another location on said container means wall;

f. determining from the record with respect to time the derivative of the decay of said induced current, said derivative having intermediate and late portions corresponding to the intermediate and late time ranges of the record;

g. examining the derivative of the decay of the record and comparing the intermediate and late time portions of the derivative to intermediate and late time portions of the derivative to intermediate and late time portions of a derivative of a reference record to determine the wall thickness of said investigated container means wall portion, said reference record obtained from a reference container means with known wall thickness, wherein said wall thickness determination of said investigated container means wall portion is unaffected by said variations in distance and wherein the presence or absence of corrosion on said investigated container means wall portion can be inferred.

2. The method of claim 1 wherein the derivative of the decay of said induced current becomes releatively constant for a portion of the derivative, further comprising the step of determining the thickness of said investigated container means wall portion by comparing the relatively constant portion of said derivative to a relatively constant portion of said reference derivative.

3. A method of measuring wall thickness to detect irregularities such as corrosion on electrically conductive walls of container means, comprising the steps of:

a. providing transmitting antenna means, receiving antenna means, transmitter means connected with said transmitting antenna means, and receiver means connected with said receiving antenna means;

b. placing said transmitting antenna means and said receiving antenna means in proximity to that portion of the container means wall which is to be investigated for irregularities;

c. providing an abruptly changing current to said transmitting antenna means from said transmitter means so as to induce current into the investigated container means wall portion;

d. detecting said induced current in said investigated container means wall portion with said receiving antenna means and said receiver means to produce a first received signal, said first received signal decaying into noise over a period of time, said first received signal having intermediate and late time ranges, said received signal being influenced by variations in distance between said transmitting and receiving antenna means and said container means wall, which variations are caused by moving said transmitting antenna means and said receiving antenna means from one location to another along said container means wall;

e. determining with respect to time the derivative of the received signal, said derivative having intermediate and late portions corresponding to the intermediate and late time ranges of said received signal;

f. comparing the intermediate and late time portions of the derivative of said received signal to intermediate and late time portions of a derivative of a reference received signal to determine the wall thickness of said investigated container means wall portion, said reference signal being obtained from a reference container means with known wall thickness, wherein the wall thickness of said investigated container means wall portion is determined without being influenced by variations in distance between the transmitting and receiving antenna means and the container means walls and the presence or absence of irregularities on the investigated container means wall portion can be determined.

4. The method of claim 3 wherein said derivative of said received signal is a logarithmic derivative.

5. The method of claim 3 further comprising the step of determining that portion of the derivative of the received signal in which the second derivative of the received signal is relatively constant, said relatively constant second derivative occurring in the late time range of said received signal, and comparing the relatively constant portion of the second derivative of the received signal to a relatively constant portion of the second derivative of said reference signal to determine the wall thickness of said investigated container means wall portion, wherein if the relatively constant portion of the second derivative of the received signal occurs earlier in time than the relatively constant portion of the second derivative of said reference signal then the wall thickness of the investigated container means wall portion is thinner than the wall thickness of said reference container means.

6. The method of claim 5 wherein said transmitting antenna means and said receiving antenna means comprise a coincident antenna arrangement.

7. The method of claim 5 wherein said container means wall is provided with a layer of insulation, said insulation being located adjacent to said container means wall so as to be interposed between said container means wall portion and said transmitting antenna means and said receiving antenna means, wherein said transmitting antenna means induces current into the investigated container means wall portion through said insulation and said receiving antenna means detects said induced current through said insulation.

8. The method of claim 5 wherein said container means wall is provided with a layer of insulation and a conductive jacket, said insulation and said jacket being located adjacent to said container means wall such that the insulation is interposed between said container means wall and said jacket, said jacket being interposed between said insulation and said transmitting antenna means and said receiving antenna means, wherein said transmitting antenna means induces current into the container means wall portion through said insulation and said jacket and said receiving antenna means detects said induced current through said insulation and said jacket.

9. The method of claim 3 wherein said container means wall is provided with a layer of insulation, said insulation being located adjacent to said container means wall so as to be interposed between said container means wall portion and said transmitting antenna means and said receiving antenna means, wherein said transmitting antenna means induces current into the investigated container means wall portion through said insulation and said receiving antenna means detects said induced current through said insulation.

10. The method of claim 3 wherein said container means wall is provided with a layer of insulation and a conductive jacket, said insulation and said jacket being located adjacent to said container means wall such that the insulation is interposed between said container means wall and said jacket, said jacket being interposed between said insulation and said transmitting antenna means and said receiving antenna means, wherein said transmitting antenna means induces current into the container means wall portion through said insulation and said jacket and said receiving antenna means detects said induced current through said insulation and said jacket.

* * * * *

UNITED STATES PATENT AND TRADEMARK OFFICE
CERTIFICATE OF CORRECTION

PATENT NO. : 4,843,319
DATED : June 27, 1989
INVENTOR(S) : Pedro F. Lara

It is certified that error appears in the above—identified patent and that said Letters Patent is hereby corrected as shown below:

In the Claims, in claim 1, col. 10, line 49, delete "near surface" and insert --near surfaces--;

also in claim 1, col. 11, lines 14-15, delete "the derivative to intermediate and late time portions of".

Signed and Sealed this

Fifteenth Day of January, 1991

Attest:

HARRY F. MANBECK, JR.

*Attesting Officer*      *Commissioner of Patents and Trademarks*